(12) United States Patent
Freiman et al.

(10) Patent No.: US 10,769,780 B2
(45) Date of Patent: Sep. 8, 2020

(54) COLLATERAL FLOW MODELLING FOR NON-INVASIVE FRACTIONAL FLOW RESERVE (FFR)

(71) Applicant: KONINKLIJKE PHILIPS N.V., Eindhoven (NL)

(72) Inventors: Mordechay Pinchas Freiman, Zichron-Yaakov (IL); Liran Goshen, Pardes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 204 days.

(21) Appl. No.: 15/768,162

(22) PCT Filed: Oct. 17, 2016

(86) PCT No.: PCT/EP2016/074852
§ 371 (c)(1),
(2) Date: Apr. 13, 2018

(87) PCT Pub. No.: WO2017/076620
PCT Pub. Date: May 11, 2017

(65) Prior Publication Data
US 2018/0315184 A1 Nov. 1, 2018

Related U.S. Application Data

(60) Provisional application No. 62/251,417, filed on Nov. 5, 2015.

(51) Int. Cl.
*G06T 7/00* (2017.01)
*A61B 6/00* (2006.01)
(Continued)

(52) U.S. Cl.
CPC ............ *G06T 7/0012* (2013.01); *A61B 5/026* (2013.01); *A61B 5/02007* (2013.01);
(Continued)

(58) Field of Classification Search
CPC ......... G06T 7/0012; G06T 7/11; G06T 15/08; A61B 6/032; A61B 6/481; A61B 6/486; A61B 6/504; A61B 6/507; A61B 6/5217
See application file for complete search history.

(56) References Cited

U.S. PATENT DOCUMENTS

| 8,157,742 B2 | 4/2012 | Taylor |
| 8,200,466 B2 | 6/2012 | Spilker |

(Continued)

FOREIGN PATENT DOCUMENTS

| DE | 102008014792 | 6/2009 |
| EP | 3062248 | 8/2016 |

(Continued)

OTHER PUBLICATIONS

Marco et al: "Rapid Decline of Collateral Circulation Increases Susceptibility to Myocardial Ischemia the Trade-Off of Successful Percutaneous Recanalization of Chronic Total Occlusions", Journal of the American College of Cardiology, vol. 48, No. 1, Jul. 4, 2006.

(Continued)

*Primary Examiner* — Bobbak Safaipour
(74) *Attorney, Agent, or Firm* — Larry Liberchuk (57) ABSTRACT

A method includes obtaining volumetric image data that includes a coronary vessel of a subject. The method further includes identifying the coronary vessel in the volumetric image data. The method further includes identifying a presence of a collateral flow for the identified coronary vessel. The method further includes determining a boundary condition of the collateral flow. The method further includes constructing a boundary condition parametric model that includes a term that represents the boundary condition of the collateral flow. The method further includes determining a fractional flow reserve index for the coronary vessel with the boundary condition parametric model.

18 Claims, 5 Drawing Sheets

(51) Int. Cl.

| | | |
|---|---|---|
| *A61B 6/03* | (2006.01) | |
| *G06T 15/08* | (2011.01) | |
| *G06T 7/11* | (2017.01) | |
| *A61B 5/0285* | (2006.01) | |
| *A61B 5/026* | (2006.01) | |
| *A61B 5/02* | (2006.01) | |
| *G16H 50/30* | (2018.01) | |
| *G16H 50/50* | (2018.01) | |
| *G16H 30/40* | (2018.01) | |
| *G06T 19/20* | (2011.01) | |

(52) U.S. Cl.
CPC ........ *A61B 5/02028* (2013.01); *A61B 5/0285* (2013.01); *A61B 6/032* (2013.01); *A61B 6/481* (2013.01); *A61B 6/486* (2013.01); *A61B 6/503* (2013.01); *A61B 6/504* (2013.01); *A61B 6/507* (2013.01); *A61B 6/5217* (2013.01); *G06T 7/11* (2017.01); *G06T 15/08* (2013.01); *G16H 30/40* (2018.01); *G16H 50/30* (2018.01); *G16H 50/50* (2018.01); *G06T 19/20* (2013.01); *G06T 2207/10081* (2013.01); *G06T 2207/30048* (2013.01); *G06T 2207/30104* (2013.01)

(56) References Cited

U.S. PATENT DOCUMENTS

| | | | |
|---|---|---|---|
| 8,249,815 | B2 | 8/2012 | Taylor |
| 9,339,200 | B2 * | 5/2016 | Fonte ............... A61B 6/507 |
| 2007/0078352 | A1 | 4/2007 | Pijls |
| 2010/0125197 | A1 | 5/2010 | Fishel |
| 2010/0130878 | A1 | 5/2010 | Lasso |
| 2010/0241404 | A1 | 9/2010 | Taylor |
| 2010/0286537 | A1 | 11/2010 | Pijls |
| 2011/0211742 | A1 | 9/2011 | Bredno |
| 2011/0307231 | A1 | 12/2011 | Kirchner |
| 2012/0022843 | A1 | 1/2012 | Ionasec |
| 2012/0041318 | A1 | 2/2012 | Taylor |
| 2012/0041319 | A1 | 2/2012 | Taylor |
| 2012/0041320 | A1 | 2/2012 | Taylor |
| 2012/0041321 | A1 | 2/2012 | Taylor |
| 2012/0041322 | A1 | 2/2012 | Taylor |
| 2012/0041323 | A1 | 2/2012 | Taylor |
| 2012/0041324 | A1 | 2/2012 | Taylor |
| 2012/0041325 | A1 | 2/2012 | Taylor |
| 2012/0041739 | A1 | 2/2012 | Taylor |
| 2012/0053918 | A1 | 3/2012 | Taylor |
| 2012/0053919 | A1 | 3/2012 | Taylor |
| 2012/0059246 | A1 | 3/2012 | Taylor |
| 2012/0072190 | A1 | 3/2012 | Sharma |
| 2012/0121151 | A1 | 5/2012 | Bernhardt |
| 2012/0238888 | A1 | 9/2012 | Bredno |
| 2012/0243761 | A1 | 9/2012 | Senzig |
| 2012/0296199 | A1 | 11/2012 | Kim |
| 2013/0132054 | A1 | 5/2013 | Sharma |
| 2014/0114618 | A1 | 4/2014 | Fonte |
| 2014/0200867 | A1 | 7/2014 | Lavi |
| 2015/0051888 | A1 | 2/2015 | Itu |
| 2015/0112191 | A1 | 4/2015 | Gilboa |
| 2015/0265162 | A1 | 9/2015 | Lavi |
| 2015/0339847 | A1 * | 11/2015 | Benishti ............. G16H 30/20 382/131 |

FOREIGN PATENT DOCUMENTS

| | | |
|---|---|---|
| WO | 00/72037 | 11/2000 |
| WO | 2004025572 | 3/2004 |
| WO | 200661814 | 6/2006 |
| WO | 200661815 | 6/2006 |
| WO | 201022762 | 3/2010 |
| WO | 2014072861 | 5/2014 |
| WO | 2014/088103 | 6/2014 |
| WO | 2016001017 | 1/2016 |

OTHER PUBLICATIONS

Demer, et al., "Assessing stenosis severity: Coronary flow reserve, collateral function, quantitative coronary arteriography, positron imaging, and digital subtraction angiography. A review and analysis". Progress in Cardiovascular Diseases, Saunders, Philadelphia, PA, US, vol. 30, No. 5, Mar. 1, 1988.

Ladwiniec Andrew et al: "The haemodynamic effects of collateral donation to a chronic total occlusion: implications for patient management", International Journal of Cardiology, vol. 198, Nov. 1, 2015.

Huffman: "Problems of Coronary Flow Reserve", Annals of Biomedical Engineering, Kluwer Academic Publishers-Plenum Publishers, NE, vol. 28, No. 8, Aug. 1, 2000.

Zarins, et al., "Computed Fractional Flow Reserve (FFTCT) Derived from Coronary CT Angiography"; J. of Cardiovasc. Trans. Res. (2013) 6:708-714.

Koo et al., "Diagnosis of ischemia-causing coronary stenoses by noninvasive fractional flow reserve computed from coronary computed tomographic angiograms. Results from the prospective multicenter DISCOVER-FLOW (Diagnosis of Ischemia-Causing Stenoses Obtained Via Noninvasive Fractional Flow Reserve) study," Journal of the American College of Cardiology, 58 (19), pp. 1989 to 1997 (2011).

Kim et al., "Patient-specific modeling of blood flow and pressure in human coronary arteries," Annals of Biomedical Engineenng 38(10), pp. 3195 to 3209 (2010).

Vignon-Clementel et al., "Outflow boundary conditions for three-dimensional simulations of non-periodic blood flow and pressure fields in deformable arteries," 13(5), pp. 625 to 640 (2010).

Finegold, et al.,: "Mortality from ischaemic heart disease by country, region, and age: Statistics from World Health Organisation and United Nations", Int J Cardiol 168(2), 934-945 (2013).

Arbab-Zadeh, et al. : "Quantification of coronary arterial stenoses by multidetector CT angiography in comparison with conventional angiography methods, caveats, and implications". JACC Cardiovasc Imaging 4(2), 191-202 (2011).

Meijboom, W., et al.: "Comprehensive assessment of coronary artery stenoses: computed tomography coronary angiography versus conventional coronary angiography and correlation with fractional flow reserve in patients with stable angina"; J Am Coll Cardiol 52(8), 636-643 (2008).

Nørgaard, B., et al: "Diagnostic performance of noninvasive fractional flow reserve derived from coronary computed tomography angiography in suspected coronary artery disease: the NXT trial (Analysis of Coronary Blood Flow Using CT Angiography: Next Steps"; J Am Coll Cardiol 63(12), 1145-1155 (2014).

Coenen, A., et al.: "Fractional Flow Reserve Computed from Noninvasive CT Angiography Data: Diagnostic Performance of an On-Site Clinician-operated Computational Fluid Dynamics Algorithm"; Radiology 274(3), 674-683 (2015).

Huo, et al., "Intraspecific scaling laws of vascular trees". J. R. Soc. Interface published online Jun. 15, 2011.

Wustmann, K., et al. "Is there functional collateral flow during vascular occlusion in angiographically normal coronary arteries?"; Circulation 107(17): 2213-2220 (2003).

* cited by examiner

COLLATERAL FLOW MODELLING FOR NON-INVASIVE FRACTIONAL FLOW RESERVE (FFR)

CROSS REFERENCE TO RELATED APPLICATIONS

This application is the U.S. National Phase application under 35 U.S.C. § 371 of International Application No. PCT/EP2016/074852, filed Oct. 17, 2016, published as WO 2017/076620 on May 11, 2017, which claims the benefit of U.S. Provisional Patent Application Number 62/251,417 filed Nov. 5, 2015. These applications are hereby incorporated by reference herein.

FIELD OF THE INVENTION

The following generally relates to non-invasive fractional flow reserve (FFR) and more particularly to collateral flow modelling for non-invasive FFR, and is described with particular application to computed tomography (CT). However, the following is also amenable to other imaging modalities including X-ray, magnetic resonance imaging (MRI), and/or other imaging modalities.

BACKGROUND OF THE INVENTION

FFR is an index of the functional severity of a coronary stenosis that is calculated from pressure measurements made during coronary arteriography and is defined as the distal blood pressure (behind a stenosis) relative to the proximal pressure (close to the Ostium) under hyperemic conditions (i.e. the ratio between the pressure after a lesion and the normal pressure). In other words, FFR expresses the maximal flow down a vessel in the presence of a stenosis compared to the maximal flow in the hypothetical absence of the stenosis. An FFR value is an absolute number between 0 and 1, where a value 0.50 indicates that a given stenosis causes a 50% drop in blood pressure, and facilitates diagnosis of the extent of a stenosis.

Computed Tomography Coronary Angiography (CCTA) is a non-invasive technique for the evaluation of coronary artery disease (CAD). The high negative predictive value in CAD detection positions CCTA as a non-invasive technique to rule out CAD in symptomatic patients with low to intermediate pre-test probability of disease. However, the literature indicates CCTA is limited in assessing hemodynamic significance of coronary lesions. Assessing hemodynamic significance from CCTA requires accurate segmentation of the coronaries to generate the three-dimensional model for flow simulations and a boundary conditions model that models the interface with the non-imaged vasculature. While many automatic and semi-automatic tools are available for generating the 3D model of the coronary tree from the CCTA data, accurate modelling of the boundary condition remains a significant challenge.

FFR-CT has the potential to improve CCTA specificity by adding hemodynamic significance assessment from CCTA data. It is known how to couple analytic models such as resistance, impedance and the Windkessel model to the boundaries of the truncated computational domain. However, these methods use constant parameters based on empirical measurements. In practice, there is a large variability between measurements of different individuals. Moreover, several studies show that the capillaries' resistance is auto-regulated to account for presence of stenosis in the parent coronary. An adaptive resistance FFR-CT model that accounts for auto-regulated changes in the capillaries' resistance due to the presence of coronary stenosis is described in PCT application PCT/EP2015/064168, filed on Jun. 24, 2015, and entitled "Apparatus for determining a fractional flow reserve value," which is incorporated by reference herein in its entirety.

Collateral flow is an auto-regulation mechanism used by the body to prevent ischemia in case of coronary stenosis by creating new arterioles that support collateral blood flow to the potentially ischemic region. The literature indicates that even in the absence of obstructive coronary artery disease or in entirely normal hearts, there has been collateral flow to a briefly occluded coronary artery sufficient to prevent ECG signs of myocardial ischemia in 20-25% of the population studied. However, due to the small diameter of the collateral arterioles CCTA cannot directly depict the presence of collateral arterioles that support collateral blood flow. As a result, currently used boundary conditions models do not account for the presence of collateral flow. Unfortunately, this may cause inaccurate estimation of the FFR values.

SUMMARY OF THE INVENTION

Aspects described herein address the above-referenced problems and others.

In one aspect, a method includes obtaining volumetric image data that includes a coronary vessel of a subject. The method further includes identifying the coronary vessel in the volumetric image data. The method further includes identifying a presence of a collateral flow for the identified coronary vessel. The method further includes determining a boundary condition of the collateral flow. The method further includes constructing a boundary condition parametric model that includes a term that represents the boundary condition of the collateral flow. The method further includes determining a fractional flow reserve index for the coronary vessel with the boundary condition parametric model.

In another aspect, a system includes an imager and a console. The image is configured to scan a subject and generate volumetric coronary angiography image data. The console is configured to control the imager. The console includes a memory with instructions for computing a fractional flow reserve and a processor configured to execute the instructions. The instructions, when executed by the processor, causes the processor to: segment a coronary vessel in the volumetric coronary angiography image data, determine whether a collateral flow for the coronary vessel is present, determine a boundary condition of the collateral flow in response to determining a presence of the collateral flow, wherein the boundary condition of the collateral flow models a resistance of the collateral flow, obtain a boundary condition parametric model for the coronary vessel, adapt the boundary condition parametric model with the boundary condition of the collateral flow, and compute a fractional flow reserve index for the coronary vessel with the boundary condition parametric model.

In another aspect, a non-transitory computer readable medium is encoded with computer executable instructions which when executed by a processor cause the processor to: locate a coronary vessel in volumetric image data, determine a presence of a collateral flow for the coronary vessel, determine a resistance boundary condition of the collateral flow, construct a boundary condition parametric model that includes the resistance boundary condition of the collateral flow and a resistance of an outlet of the coronary vessel, and determine a fractional flow reserve index for the coronary vessel with the boundary condition parametric model.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
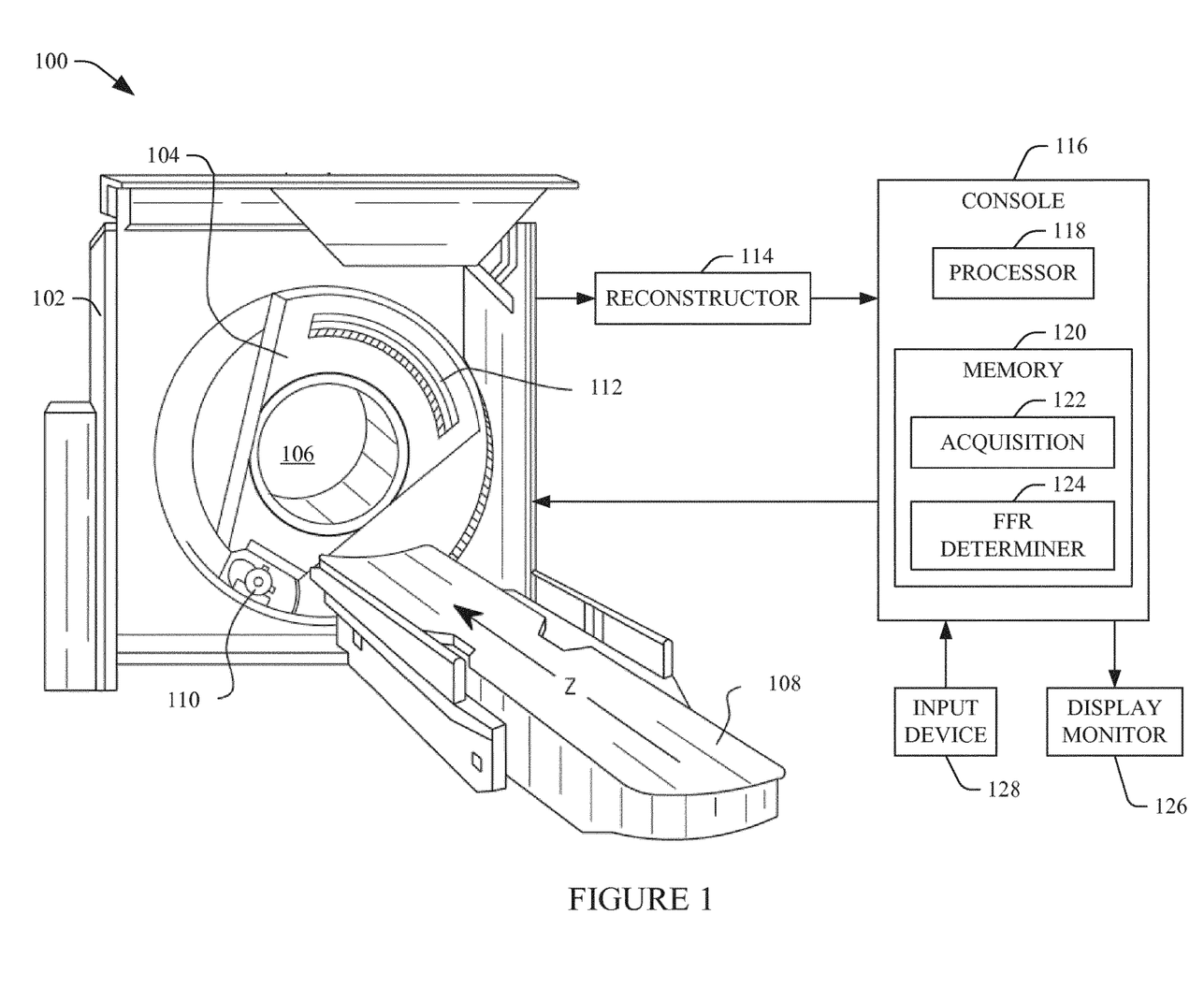
FIG. 1 schematically illustrates a system with a fractional flow reserve determiner.

FIG. 1 schematically illustrates an imaging system 100 such as a computed tomography (CT) scanner. In this example, the imaging system 100 is configured at least for coronary CT angiography (CCTA) scans or procedures. In another embodiment, the imaging system 100 additionally or alternatively includes an X-ray scanner, magnetic resonance imaging (MRI) scanner, and/or other scanner configured coronary CT angiography (CCTA) and/or other scans.

A stationary gantry 102 rotatably supports a rotating gantry 104, which is configured to rotate around an examination region 106. A subject support 108 supports an object or subject in the examination region 106. A radiation source 110, such as an x-ray tube, is supported by the rotating gantry 104, rotates with the rotating gantry 104, and is configured to emit radiation that traverses the examination region 106.

A radiation sensitive detector array 112 subtends an angular arc opposite the radiation source 110 across the examination region 106, and is configured to detect radiation traversing the examination region 106 and generate a signal (projection data) indicative thereof. A reconstructor 114 is configured to reconstruct the projection, generating volumetric image data indicative of a scanned portion of a subject or object located in the examination region 106.

For CCTA procedures, the subject is administered (e.g., intravenously, etc.) a radio-opaque contrast agent and the resulting volumetric image data is CCTA image data that visualizes the inside (lumen) of blood vessels such as arteries, veins, etc. of a coronary vessel and/or other vessel.

A computing system serves as a console 116 for the imaging system 100. The console 116 includes at least one processor 118 (e.g., a microprocessor, a central processing unit, etc.) that executes at least one computer readable instruction stored in a computer readable storage medium ("memory") 120, which excludes transitory medium and includes physical memory and/or other non-transitory medium.

The at least one computer readable instruction, in this example, includes an acquisition module 122 and an FFR determiner 124. In a variation, the FFR determiner 124 is stored in a memory of and executed with a processor of a computing system different from the console 116 such as a workstation, computer, etc. An output device(s) includes a human readable output device such as a display monitor 126, and an input device(s) 128 includes a mouse, keyboard, touchscreen, etc.

The data acquisition module 122 includes instructions for performing a scan and reconstructing CCTA image data. The FFR determiner 124 includes instructions for determining an FFR from CCTA image data. As described in greater detail below, in one instance this includes detecting whether a collateral flow for a coronary vessel is present from the CCTA image data based on indirect analysis of voxel intensity (e.g., Hounsfield unit (HU) values) along the coronary tree.

A machine learning approach is used to characterize the presence of collateral flow from the CCTA image data and to find the relationship between the presence of collateral flow and boundary condition parametric model parameters. The FFR determiner 124 employs an algorithm that includes an adaptive boundary condition model that accounts for a presence of a collateral flow and/or adapts a boundary condition model as such.

This approach allows for patient specific FFR-CT analysis that accounts for collateral flow and the unique anatomical and physiological features of each patient, which can lead to an improved FFR estimation, relative to a configuration in which collateral flow is not taken into account.

Figure 2:
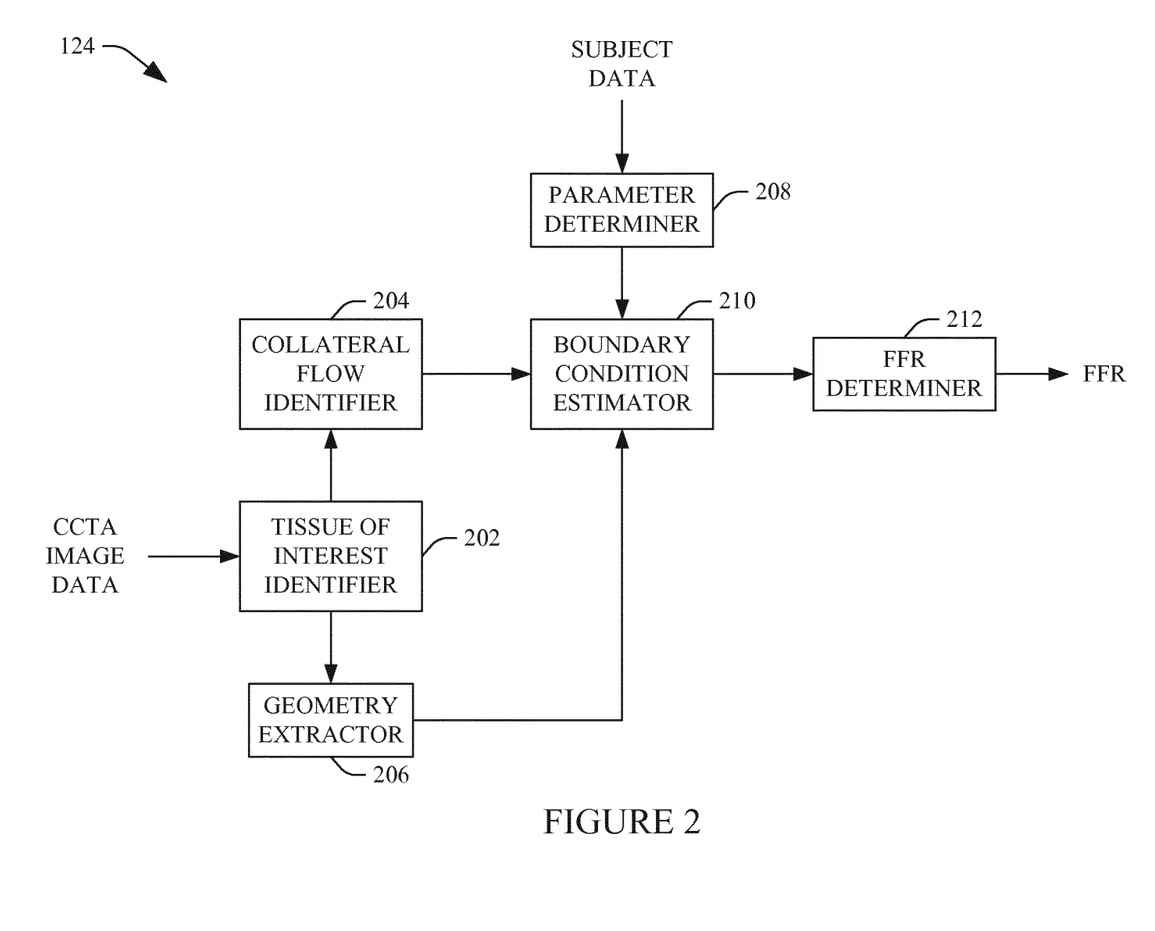
FIG. 2 illustrates an example of the fractional flow reserve determiner.

FIG. 2 illustrates an example of the FFR determiner 124.

A tissue of interest identifier 202 identifies tissue of interest in the volumetric image data. The tissue of interest can be identified by a user, a default tissue of interest, etc. The tissue of interest identifier 202 can employ automatic and/or manual approaches to identify the tissue of interest. In the illustrated example, the tissue of interest is a vessel such as a coronary vessel and/or other vessel.

A collateral flow identifier 204 is configured to identify whether there is collateral flow for the tissue of interest. For a coronary vessel, collateral flow is an auto-regulation mechanism used by the body to prevent ischemia in case of coronary stenosis by creating new arterioles that support collateral blood flow to the potentially ischemic region. Collateral flow can be characterized by magnitude (e.g., poorly developed vs well-developed collateral arterioles) and direction (e.g., retrograde vs antegrade) from the coronary ostium, which is the opening of coronary arteries at root of aorta, superior to the aortic valve.

In this example, the collateral flow identifier 204 assesses collateral flow magnitude and/or direction indirectly from the CCTA image data by analyzing changes in the voxel intensity (e.g., in HUs) along the coronary vessel as a function of a distance from the ostium. For this, in one instance, the collateral flow identifier 204 automatically extracts a vessel centerline and the lumen. This can be achieved through known and/or other approaches. Next, a machine-learning approach characterizes the magnitude and the direction of the collateral flow based on the centerline and the lumen.

In an example approach, the collateral flow identifier 204 estimates average HUs in equidistant points along a centerline I(c). For this, the collateral flow identifier 204 first fits a second order polynomial function to the measurements. A non-limiting example of a suitable fitting of a second order polynomial function $I_p(c)$ based on a least-square approach is shown in EQUATION 1:

$$\widehat{I_p(c)} = \operatorname{argmin} \sum_{c \in C} (I_p(c) - I(c))^2. \qquad \text{EQUATION 1}$$

Other approaches are also contemplated herein. Next, the collateral flow identifier 204 estimates the magnitude and the direction of the collateral flow by analyzing the polynomial function coefficients and its derivatives respectively to determine the magnitude and the direction.

Examples of antegrade and retrograde collateral flow and corresponding polynomial functions are shown in connection with FIGS. 3, 4, 5 and 6.

Figure 3:
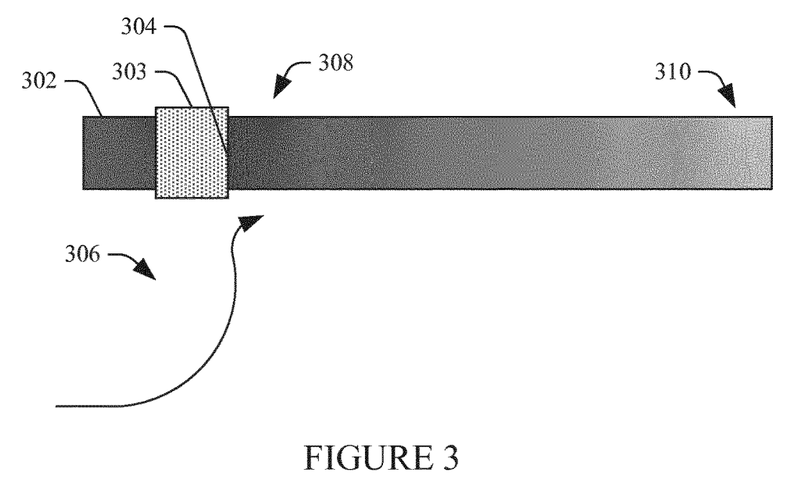
FIG. 3 shows an example vessel with antegrade collateral flow.
Figure 4:
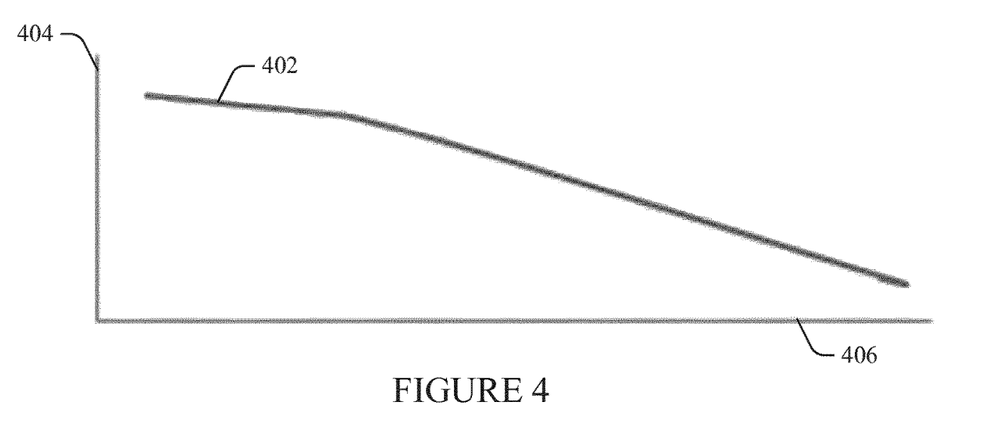
FIG. 4 shows a plot of a polynomial function fitted to voxel intensity values and as a function of distance along a coronary vessel from the ostium for antegrade collateral flow.

FIG. 3 shows an example vessel 302, a total occlusion 303, an ostium 304, and antegrade collateral flow 306, where flow is greater in a darker gray region 308 proximal the ostium 304 and flow is lower in a lighter gray region 310 distal the ostium 304. FIG. 4 shows an example of a plot 402 of a polynomial function for FIG. 3 that indicates a presence of the antegrade collateral flow. A first axis 404 represents intensity (e.g., in HU) and a second axis 406 represents distance from the Ostium (e.g., in mm). The concave shape of the plot 402 indicates antegrade flow.

Figure 5:
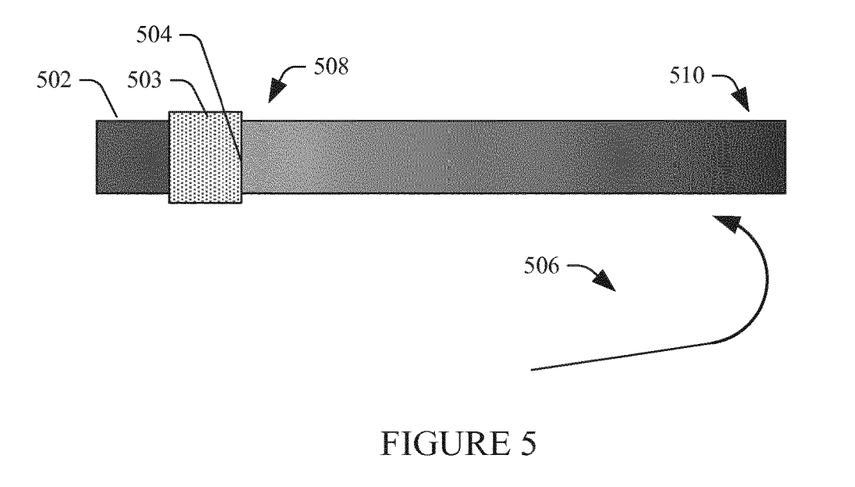
FIG. 5 shows an example vessel with retrograde collateral flow.
Figure 6:
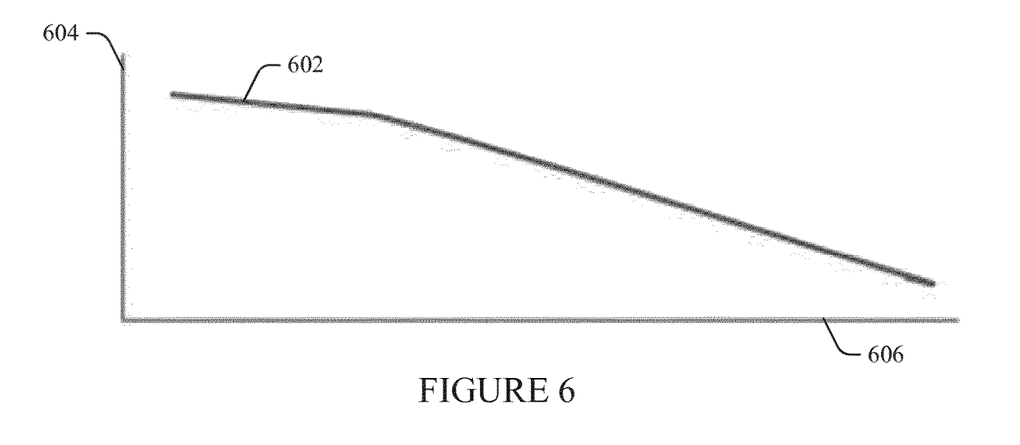
FIG. 6 shows a plot of a polynomial function fitted to voxel intensity values and as a function of distance along a coronary vessel from the ostium for retrograde collateral flow.

FIG. 5 shows an example vessel 502, a total occlusion 503, an ostium 504, and retrograde collateral flow 504, where flow is lower in a lighter gray region 508 proximal the ostium 304 and flow is greater in a darker gray region 510 distal the ostium. FIG. 6 shows an example of a plot 602 of a polynomial function for FIG. 5 that indicates a presence of the retrograde collateral flow. A first axis 604 represents intensity (e.g., in HU) and a second axis 606 represents distance from the Ostium (e.g., in mm). The convex shape of the plot 602 indicates retrograde flow.

Generally, if collateral flow were absent, the plots 402 and 602 would be horizontal lines, and not concave nor convex, as shown respectively in FIGS. 4 and 6, and the flow would be the same from the regions 308 and 508 respectively to the regions 310 and 510 (the same shade of gray), unlike that in FIGS. 3 and 5.

Returning to FIG. 2, a geometry extractor 206 extracts geometrical information from the identified tissue of interest. The geometry extractor 206 can employ automatic and/or manual approaches to extract the geometrical information. By way of example, the extraction may include employing a segmentation algorithm. From this and/or other extraction, an effective diameter at the ostium $d_o$ and/or other tissue of interest geometry can be determined.

A parameter determiner 208 determines a parameter based on input subject data. For example, the parameter determiner 208 can determine an inlet flow-rate $Q_o$ (i.e., flow rate at the ostium). This can be achieved based on subject data such as weight, body mass index (BMI), gender, age, blood test results, anatomical imaging data (e.g., myocardium mass and estimated stroke-volume), and/or subject data.

A boundary condition estimator 210 estimates boundary conditions such as flow, pressure, resistance, etc., taking into account collateral flow, if collateral flow is identified by the collateral flow identifier 204. In one instance, the boundary condition estimate is a resistance and is combined with a resistance boundary condition of the coronary vessel. For example, a flow rate Q can be determined at the outlet of a coronary vessel as a function of the coronary outlet cross sectional area, as shown in EQUATION 2:

$$Q = Q_o \left(\frac{d}{d_o}\right)^{\frac{7}{3}}, \qquad \text{EQUATION 2}$$

where $Q_o$ and $d_o$ are described above and d is an effective diameter at the outlet. The effective diameter at the outlet d can be computed as shown in EQUATION 3:

$$d = 2\sqrt{\frac{csa}{\pi}}, \qquad \text{EQUATION 3}$$

where csa is a cross-sectional area of the vessel at the outlet.

A similar relationship can be derived to describe a flow split of two branches of the coronary tree based on their respective diameters as shown in EQUATION 4:

$$\frac{Q_1}{Q_2} = \left(\frac{d_1}{d_2}\right)^{\frac{7}{3}} \qquad \text{EQUATION 4}$$

where a subscript "1" represents one of the two branches and a subscript "2" represents the other of the two branches. Dividing this relationship by a pressure before the bifurcation yields a relationship between resistances of the two branches to flow as shown in EQUATION 5:

$$\frac{R_1}{R_2} = \left(\frac{d_1}{d_2}\right)^{-\frac{7}{3}} \qquad \text{EQUATION 5}$$

where $R_1$ is a resistance of one of the two branches and $R_2$ is a resistance of the other of the two branches. In general, these resistances are dominated by peripheral microvascular arteries with diameters lower than 0.2 mm.

The influence of stenosis on the resistance can be formulated as summation of the normal outlet resistance and additional resistance component which can be modeled as linearly related to the normal resistance as shown in EQUATION 6.

$$R_s = R_0 + \varepsilon R_0, \qquad \text{EQUATION 6}$$

where $R_s$ is the assigned outlet resistance adjusted from normal outlet resistance to account for the presence of stenosis, $R_0$ is the normal resistance at the outlet and E is represents an amount of stenosis in the coronary vessel of interest. The normal outlet resistance and the parameter £ can be found by optimizing an error function over a training set with invasive FFR measurements as the ground-truth.

The influence of the collateral flow can be integrated into this model. In one approach, this includes a virtual addition of arterioles to the three-dimensional geometrical model of the coronary tree in the amount and direction of the collateral flow. In another approach, this includes an adjustment of the coronaries outlets' resistance values to reflect the presence of collateral flow.

For example, the latter may include using a linear model shown in EQUATION 7:

$$R_c = R_s + \alpha F_c, \qquad \text{EQUATION 7}$$

where $R_c$ represents adjusted resistance accounting for the collateral flow, $R_s$ is the coronary outlet resistance computed using a suitable boundary conditions model (e.g., as described in patent application PCT/EP2015/064168), $F_c$ represents a collateral flow as determined by the collateral flow identifier 204 and/or otherwise, and a represents a weighting parameter.

The parameter α is a free parameter, which can be optimized experimentally, e.g., by optimizing an error function over a training dataset with invasive FFR measurements as the ground-truth. For example, this can be achieved by optimizing the error function shown in EQUATION 8:

$$\hat{\alpha} = \underset{\alpha}{\text{argmin}} \sum_{C \in TrainingCases} (\text{FFR\_CT}(C, F_c) - \text{FFR\_GT}(C))^2. \quad \text{EQUATION 8}$$

where $\hat{\alpha}$ is the optimal value for the parameter α found through the optimization, C is the coronary model of one patient from the database (TrainingCases), $F_c$ represents a collateral flow as determined by the collateral flow identifier, FFR_CT (C, $F_c$) is the FFR value calculated based on the inputs C, $F_c$ with a given value for the parameter α, and FFR_GT(C) is the invasively measured FFR value for this patient.

In general, there are several relationships between microvascular resistance and anatomical and physiological features. Patent application PCT/EP2015/064168 describes some of the features that related to the microvascular resistance, including the coronary outlet cross-sectional area, presence of coronary stenosis, heart size, ejection fraction, among others. Different parametric relationships can be considered, including weighted linear sum or weighted non-linear sum of the different effects.

An FFR determiner 214 determines an FFR based on the boundary conditions. In one instance, this includes simulating the flow of blood within the coronary artery system based on a representation of the coronary artery system and the boundary conditions and then determining the FFR value based on the simulated flow of the blood. The FFR determiner 214 can employ zero-dimensional, one-dimensional, etc. algorithms that solve fluid dynamics problems. For example, in one instance, the FFR determiner 214 utilizes a computational fluid dynamic (CFD) simulation using partial-differential-equations. Generally, CFD is a fluid mechanics approach that uses numerical methods and/or algorithms to solve and analyze problems that involve fluid flows. The calculations are performed with surfaces defined by boundary conditions.

Examples of suitable approaches are disclosed in Koo et al., "Diagnosis of ischemia-causing coronary stenoses by noninvasive fractional flow reserve computed from coronary computed tomographic angiograms. Results from the prospective multicenter DISCOVER-FLOW (Diagnosis of Ischemia-Causing Stenoses Obtained Via Noninvasive Fractional Flow Reserve) study," Journal of the American College of Cardiology, 58 (19), pages 1989 to 1997 (2011), Kim et al., "Patient-specific modeling of blood flow and pressure in human coronary arteries," Annals of Biomedical Engineering 38(10), pages 3195 to 3209 (2010), and Vignon-Clementel et al., "Outflow boundary conditions for three-dimensional simulations of non-periodic blood flow and pressure fields in deformable arteries," 13(5), pages 625 to 640 (2010).

Again, the approach described herein allows for patient specific FFR-CT analysis that accounts for collateral flow and the unique anatomical and physiological features of each patient, which can lead to an improved FFR estimation, relative to a configuration in which collateral flow is not taken into account.

Figure 7:
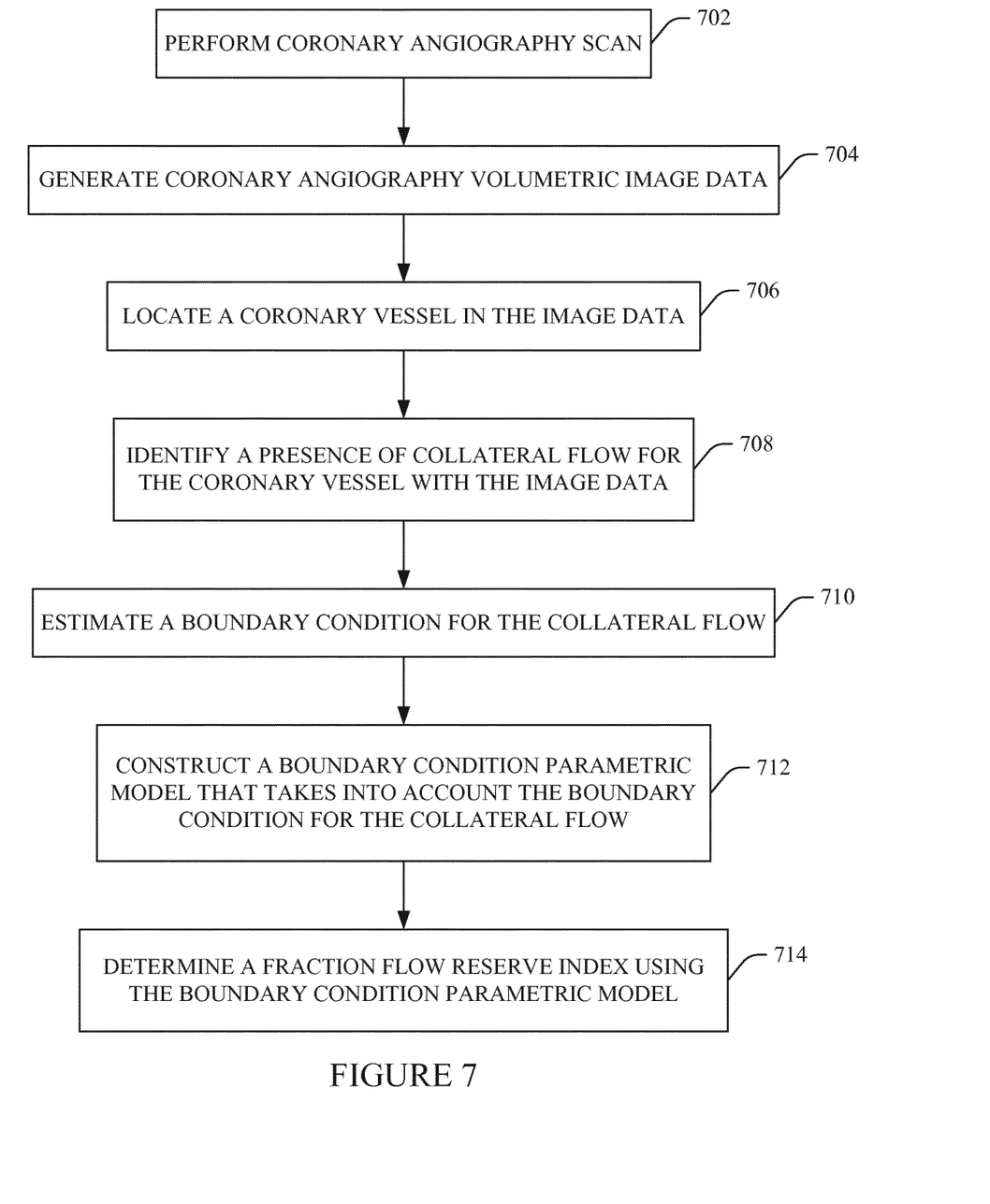
FIG. 7 illustrates an example method for determining fractional flow reserve, taking into account collateral flow.

FIG. 7 illustrates an example method for determining an FFR.

It is to be appreciated that the ordering of the above acts is not limiting. As such, other orderings are contemplated herein. In addition, one or more acts may be omitted and/or one or more additional acts may be included.

At 702, a coronary angiography scan of a subject is performed.

At 704, volumetric coronary angiography imag data is generated from the data acquired during the scan.

At 706, the volumetric coronary angiography imag data is processed to locate a coronary vessel represented in the volumetric coronary angiography imag data.

At 708, a presence of a collateral flow for the identified coronary vessel is identified with the volumetric coronary angiography imag data, as described herein and/or otherwise.

At 710, a boundary condition is estimated for the collateral flow, as described herein and/or otherwise.

At 712, a boundary condition parametric model that includes takes into account the boundary condition of the collateral flow is constructed, as described herein and/or otherwise.

At 714, a fractional flow reserve index is determined for the coronary vessel with the boundary condition parametric model.

The above may be implemented by way of computer readable instructions, encoded or embedded on non-transitory computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

What is claimed is:

1. A method, comprising:
obtaining volumetric image data that includes a coronary vessel of a subject;
identifying the coronary vessel in the volumetric image data;
identifying a presence of a collateral flow for the identified coronary vessel, including:
identifying an ostium of the coronary vessel in the volumetric image data;
identifying a centerline of the coronary vessel;
estimating a magnitude and a direction of flow in the identified coronary vessel from the ostium and along the centerline from the volumetric image data; and
identifying the presence of the collateral flow with the estimated magnitude and the estimated direction;
determining a boundary condition of the collateral flow;
constructing a boundary condition parametric model that includes a term that represents the boundary condition of the collateral flow; and determining a fractional flow reserve index for the coronary vessel with the boundary condition parametric model.

2. The method of claim 1, wherein the boundary condition of the collateral flow models a resistance of the collateral flow.

3. The method of claim 2, wherein the boundary condition parametric model further includes a term that represents a boundary condition of the coronary vessel.

4. The method of claim 3, wherein the boundary condition of the coronary vessel models a resistance of the coronary vessel.

5. The method of claim 4, wherein constructing the boundary condition parametric model includes adjusting the resistance of the coronary vessel to reflect the presence of the collateral flow based on the collateral flow.

6. The method of claim 4, wherein constructing the boundary condition parametric model includes adding virtual vasculature to the coronary vessel to represent the collateral flow, wherein the boundary condition of the coronary vessel models the resistance of the coronary vessel and the added vasculature.

7. The method of claim 1, further comprising:
estimating an average voxel intensity along the centerline from the volumetric image data; and
fitting a polynomial function to the average intensity, wherein estimating the magnitude and the direction includes determining coefficients of the fitted polynomial function and derivatives of the fitted polynomial function.

8. The method of claim 7, wherein fitting is based on a least-square approach.

9. The method of claim 7, further comprising:
identifying the collateral flow as retrograde flow in response to the fitted polynomial function being convex.

10. The method of claim 7, further comprising:
identifying the collateral flow as antegrade flow in response to the fitted polynomial function being concave.

11. The method of claim 1, wherein the volumetric image data includes computed tomography coronary angiography image data.

12. A system-, comprising:
an imager configured to scan a subject and generate volumetric coronary angiography image data;
a console configured to control the imager, wherein the console includes a memory storing instructions for computing a fractional flow reserve and a processor configured to execute the instructions, wherein executing the instructions causes the processor to:
segment a coronary vessel in the volumetric coronary angiography image data;
determine whether a collateral flow for the coronary vessel is present by:
locating an ostium of the coronary vessel in the volumetric image data;
estimating a centerline of the coronary vessel;
estimating a magnitude and a direction of flow in the coronary vessel from the ostium and along the centerline from the volumetric image data; and
determining the presence of the collateral flow with the estimated magnitude and the estimated direction;
determine a boundary condition of the collateral flow in response to determining a presence of the collateral flow, wherein the boundary condition of the collateral flow models a resistance of the collateral flow;
obtain a boundary condition parametric model for the coronary vessel;
adapt the boundary condition parametric model with the boundary condition of the collateral flow; and
compute a fractional flow reserve index for the coronary vessel with the boundary condition parametric model.

13. The system of claim 12, wherein the boundary condition of the collateral flow models a resistance the collateral flow.

14. The system of claim 13, wherein the processor adapts the boundary condition parametric model by adjusting an outlet resistance of the coronary vessel to reflect the presence of the collateral flow.

15. The system of claim 13, wherein the processor adapts the boundary condition parametric model by adding virtual vasculature to the coronary vessel to represent the collateral flow.

16. The system of claim 12, wherein the processor determines the presence of collateral flow by:
estimating an average voxel intensity along the centerline from the volumetric image data;
fitting a polynomial function to the average intensity; and
determining coefficients of the fitted polynomial function and derivatives of the fitted polynomial function.

17. The system of claim 16, wherein the processor identifies the collateral flow as retrograde flow in response to the fitted polynomial function being convex and identifies the collateral flow as antegrade flow in response to the fitted polynomial function being concave.

18. A non-transitory computer readable medium encoded with computer executable instructions which when executed by a processor cause the processor to:
locate a coronary vessel in volumetric image data;
determine a presence of a collateral flow for the coronary vessel by:
locating an ostium of the coronary vessel in the volumetric image data;
estimating a centerline of the coronary vessel;
estimating a magnitude and a direction of flow in the coronary vessel from the ostium and along the centerline from the volumetric image data; and
determining the presence of the collateral flow with the estimated magnitude and the estimated direction;
determine a resistance boundary condition of the collateral flow;
construct a boundary condition parametric model that includes the resistance boundary condition of the collateral flow and a resistance of an outlet of the coronary vessel; and
determine a fractional flow reserve index for the coronary vessel with the boundary condition parametric model.

* * * * *